(12) United States Patent
Newman et al.

(10) Patent No.: US 11,058,677 B2
(45) Date of Patent: Jul. 13, 2021

(54) LFA-1 INHIBITOR FORMULATIONS

(71) Applicant: Novartis AG, Basel (CH)

(72) Inventors: Mary Newman, Brisbane, CA (US); William Hunke, Harleysville, PA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/650,955

(22) PCT Filed: Dec. 18, 2013

(86) PCT No.: PCT/US2013/076041
§ 371 (c)(1),
(2) Date: Jun. 10, 2015

(87) PCT Pub. No.: WO2014/100135
PCT Pub. Date: Jun. 26, 2014

(65) Prior Publication Data
US 2015/0320737 A1    Nov. 12, 2015

Related U.S. Application Data

(60) Provisional application No. 61/758,147, filed on Jan. 29, 2013, provisional application No. 61/739,609, filed on Dec. 19, 2012.

(51) Int. Cl.
*A61K 31/4725* (2006.01)
*A61K 47/02* (2006.01)
*A61K 9/00* (2006.01)

(52) U.S. Cl.
CPC ........ *A61K 31/4725* (2013.01); *A61K 9/0048* (2013.01); *A61K 47/02* (2013.01)

(58) Field of Classification Search
CPC ................................................. A61K 31/4725
See application file for complete search history.

(56) References Cited

U.S. PATENT DOCUMENTS

| | | | | |
|---|---|---|---|---|
| 2,694,719 | A | 11/1954 | Jan Opplt | |
| 5,880,107 | A * | 3/1999 | Buenter | A61P 27/02 514/54 |
| 6,258,814 | B1 * | 7/2001 | Martin | A61K 9/0043 514/252.12 |
| 6,299,888 | B1 * | 10/2001 | Mizobuchi | A61P 17/00 424/401 |
| 8,084,047 | B2 * | 12/2011 | Shen | A61K 31/198 424/400 |
| 8,680,078 | B2 * | 3/2014 | Aleo | A61K 9/0048 514/96 |
| 8,877,168 | B1 * | 11/2014 | Higashiyama | A61K 9/0048 424/78.04 |
| 2005/0042284 | A1 * | 2/2005 | Hobden | A61K 31/192 424/464 |
| 2005/0288274 | A1 * | 12/2005 | Trach | A61K 9/0043 514/215 |
| 2006/0073172 | A1 * | 4/2006 | Schneider | A61K 9/0048 424/400 |
| 2009/0025957 | A1 | 1/2009 | Wallgren et al. | |
| 2009/0209632 | A1 * | 8/2009 | Isowaki | A61K 9/0048 514/450 |
| 2009/0257957 | A1 | 10/2009 | Burnier et al. | |
| 2009/0258070 | A1 | 10/2009 | Burnier et al. | |
| 2009/0298869 | A1 | 12/2009 | Burnier et al. | |
| 2010/0092542 | A1 * | 4/2010 | Burnier | A61K 31/198 424/429 |
| 2011/0152376 | A1 * | 6/2011 | Ambrus | C07C 235/30 514/622 |
| 2011/0212142 | A1 * | 9/2011 | Chaniyilparampu | A61K 9/0048 424/400 |
| 2012/0028929 | A1 * | 2/2012 | Power | A61K 9/0048 514/153 |
| 2012/0094962 | A1 * | 4/2012 | Skulachev | C09B 69/001 514/125 |
| 2012/0123162 | A1 | 5/2012 | Hwang et al. | |
| 2012/0190653 | A1 * | 7/2012 | Gilbard | A61K 31/65 514/153 |
| 2013/0317058 | A1 * | 11/2013 | Rengasamy | A61K 31/439 514/304 |

FOREIGN PATENT DOCUMENTS

| | | | | |
|---|---|---|---|---|
| CN | 103230583 A | * | 8/2013 | |
| JP | 2007506579 | | 7/1995 | |
| RU | 2149611 | | 5/2000 | |
| WO | 1993023010 | | 11/1993 | |
| WO | 2012100109 | | 7/2012 | |
| WO | WO-2013003825 A1 | * | 1/2013 | ............. A61P 29/00 |
| WO | WO-2013148896 A1 | * | 10/2013 | ............. A61P 27/02 |

OTHER PUBLICATIONS

Swarbrick, "Pharmaceutical Stress Testing" 2005 Taylor & Francis Group.*
Wu "Substituent Effects on the C—H Bond Dissociation Energy of Toluene. A Density Functional Study" J. Org. Chem. 1996, 61,746-750.*
"Guidance for Industry Q1A(R2) Stability Testing of New Drug Substances and Products" U.S. Department of Health and Human Services, Food and Drug Administration, Center for Drug Evaluation and Research (CDER), Center for Biologies Evaluation and Research (CBER) Nov. 2003.*

(Continued)

*Primary Examiner* — David K O'Dell
(74) *Attorney, Agent, or Firm* — Asha K. Nadipuram

(57) ABSTRACT

The present invention provides formulations, methods and kits for the treatment of dry eye diseases. In particular, stabilized pharmaceutical compositions comprising the compound of Formula 1 are described herein for a variety of uses including the treatment of dry eye syndrome. In one aspect, methods and ingredients for improving the stability of compositions of the compound of Formula 1 are described.

21 Claims, 12 Drawing Sheets

(56) References Cited

OTHER PUBLICATIONS

Reid D "Early prediction of pharmaceutical oxidation pathways by computational chemistry and forced degradation." Pharm Res 2004 21(9):1708-1717.*
Berge, et al., "Pharmaceutical Salts", J. Pharm. Sci. 66(1): 1-19, 1977.
Eurasian Office Action, dated Mar. 16, 2016, issued in corresponding Eurasian Patent Application No. 201591180/28.
International Search Report, dated Apr. 18, 2014, issued in corresponding International Application No. PCT/US2013/076041.
International Preliminary Report on Patentability, dated Jul. 2, 2015, issued in corresponding International Application No. PCT/US2013/076041.
Substantial Examination Report from Saudi Arabia, dated May 5, 2016, issued in corresponding Application No. 615360637 in Saudi Arabia.
Supplementary European Search Report dated Jul. 11, 2016 in connection with EPO Application No. 13865757.
Japanese Office Action dated Jul. 31, 2017 in connection with JP Application No. 2015-549612.
Eye drops—how to make it and its application—Oct. 20, 1962, p. 62-67, 87-89 (publication showing well-known technique).
Sulfacetamide Sodium Product Label (2003).
Semba et al., "A phase 2 randomized, double-masked, placebo-controlled study of a novel integrin antagonist (SAR 1118) for the treatment of dry eye," Am J Ophthalmol. 153(6):1050-60 (2012).
Pramar et al., "Compounding Ophthalmic Liquids," available at <https://cdn.ymaws.com/www.louisanapharmacists.com/resource/resmgr/imported/OPHTHALMIC%20LIQUIDS-LP.pdf>, published Oct. 10, 2009 (11 pages).

* cited by examiner

*Antioxidants*
1. Sodium bisulfite 0.2%
   /sodium thiosulfate 0.3%
2. Sodium bisulfite 0.2%
3. Sodium thiosulfate 0.3%
4. Acetylcysteine 0.2%
5. Thioglycerol 0.2%
6. Vitamin E TPGS 0.5%
7. Ascorbic Acid 0.3%

LFA-1 INHIBITOR FORMULATIONS

CROSS-REFERENCE TO RELATED APPLICATIONS

The present application is the national-stage entry of International Application No. PCT/US13/76041, filed Dec. 18, 2013, which claims priority to U.S. Provisional Application No. 61/739,609, filed Dec. 19, 2012, and U.S. Provisional Application No. 61/758,147, filed Jan. 29, 2013, both of which are herein incorporated by reference in their entireties.

BACKGROUND OF THE INVENTION

Tears provide constant moisture and lubrication to the eye, which is essential to maintain vision and comfort. Tears are a combination of water (for moisture), oils (for lubrication), mucus (for even spreading), and antibodies and special proteins (for resistance to infection). These components are secreted by special glands located around the eye. When there is an imbalance in this tear system, a person may experience dry eyes.

Dry eye syndrome is a common ocular surface inflammatory disease. A person with dry eyes may experience pain, light sensitivity, itching, redness and blurring of vision. There are several predisposing factors for dry eye syndrome including age, gender, environment, medications, surgery and systemic diseases like diabetes, thyroid disease, lymphoma, inflammatory diseases, and the like. Lack of proper diagnosis and treatment can lead to further complications like infection, ocular surface keratinization, corneal ulceration, and conjunctival squamous metaplasia.

INCORPORATION BY REFERENCE

All publications and patent applications mentioned in this specification are herein incorporated in its entirety by reference to the same extent as if each individual publication or patent application was specifically and individually indicated to be incorporated in its entirety by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Definitions

Figure 1:
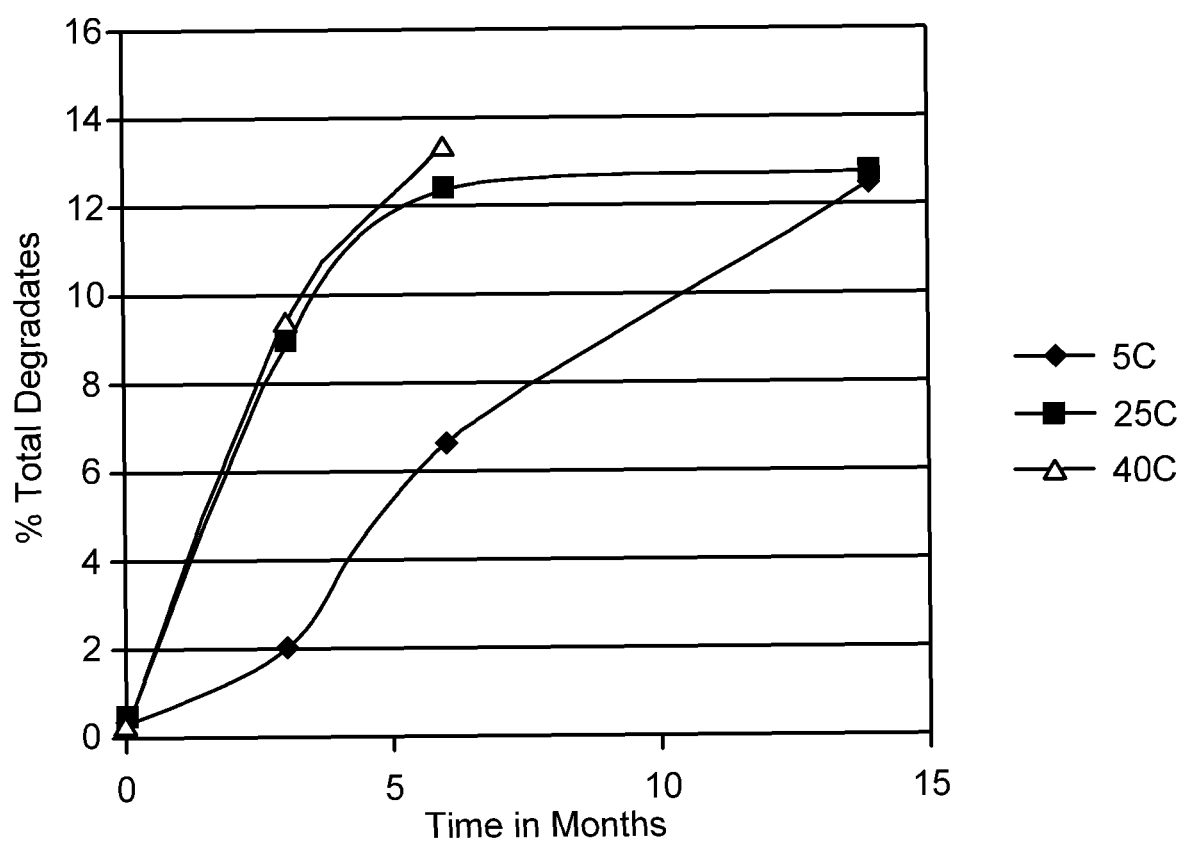
FIG. 1 shows the stability of the compound of Formula 1 in a 5.0% opthalmic solution over time at various temperatures.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. The compositions may be administered to a subject to prevent progression of physiological symptoms or to prevent progression of the underlying disorder A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

"Pharmaceutically acceptable carrier" or "pharmaceutically acceptable excipient" or "pharmaceutically acceptable ingredient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

As used herein, the term "pharmaceutically acceptable salt" refers to those salts which are suitable for pharmaceutical use, preferably for use in the tissues of humans and lower animals without undue irritation, allergic response and the like. Pharmaceutically acceptable salts of amines, carboxylic acids, and other types of compounds, are well known in the art. For example, S. M. Berge, et al., describe pharmaceutically acceptable salts in detail in J Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzoate, bisulfate, borate, butyrate, camphorate, camphorsulfonate, citrate, cyclopentanepropionate, digluconate, dodecylsulfate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, nicotinate, nitrate, oleate, oxalate, palmitate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed by direct reaction with the drug carboxylic acid or by using counterions such as halide, hydroxide, carboxylate, sulfate, phosphate, nitrate, sulfonate and aryl sulfonate. Unless otherwise indicated, reference to the compound of Formula 1 includes salts thereof.

The term "subject" as used herein, refers to an animal, such as a mammal, for example a human. The methods described herein can be useful in both human therapeutics and veterinary applications. In some embodiments, the patient is a mammal, and in some embodiments, the patient is human.

The term "primary antioxidant" as used herein, refers to an antioxidant that when present in combination with one or more other antioxidants is individually responsible for greater than 50% of the total antioxidative or stabilizing effect.

The term "essentially no" as used herein, refers to not being present in an effective amount. For example formulations comprising essentially no lubricants refer to formulations comprising of a sub-effective amount of lubricants. An effective amount is the amount of a particular substance or additive needed to achieve a noticeable change in the property for which the substance was added.

Unless otherwise stated, structures depicted herein are also meant to include compounds which differ only in the presence of one or more isotopically enriched atoms. For example, compounds having structures wherein a hydrogen atom is replaced by a deuterium or tritium, or a carbon is replaced by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{4}$C). All isotopic variations of the compounds of the present invention, whether radioactive or not, are encompassed within the scope of the present invention.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range.

The term "comprising" (and related terms such as "comprise" or "comprises" or "having" or "including") includes those embodiments, for example, an embodiment of any composition of matter, composition, method, or process, or the like. The phrase "consists essentially of" indicates that additional components do not materially affect the described features.

Abbreviations used herein have their conventional meaning within the chemical and biological arts.

I. Compound and Compositions

Compound of Formula 1

The Compound of Formula 1:

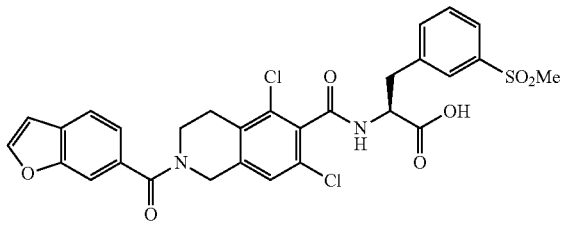

Formula 1 or a salt thereof, has been found to be an effective inhibitor of LFA-1 interactions with ICAM-1. It is a member of a class of directly competitive inhibitors of LFA-1, binding to ICAM's binding site on LFA-1 directly, and thus excludes ICAM binding. Directly competitive inhibitors of LFA-1 may offer the potential for more effective modulation of the inflammatory and/or immunologic response than allosteric inhibitors provide, precisely because these inhibitors occlude the binding site more effectively.

Additionally, the compound of Formula 1 has a rapid systemic clearance rate. LFA-1 interactions with ICAMs exert various systemic effects throughout the body. Treatment of a disorder using an LFA-1 antagonist may result in unwanted effects due to LFA-1 antagonist activity in unwanted locations, for example, other than at the site of administration. The present invention utilizes the compound of Formula 1 which is cleared quickly from systemic circulation. The compound of Formula 1 may have minimal systemic LFA-1 antagonist activity. In some embodiments, the compound of Formula 1 may have undetectable systemic LFA-1 antagonist activity. Therefore, the compound of Formula 1 may be particularly well suited for treatment of a disorder mediated by the interaction between LFA-1 and ICAM-1, where localized treatment is desirable and/or where such localized treatment is administered for many months or years.

In order to develop clinically useful therapeutics, drug candidates need to be readily accessible (by synthetic or other means), chemically pure and of an acceptable physical form suitable administration into a subject. Developing a stable formulation of a drug candidate requires thorough investigation of the intrinsic stability of the compound. The drug candidates also need to be tested for compatibility with relevant excipients and low risk excipients need to be identified.

The current invention discloses methods and compositions to access stable pharmaceutical formulations of the compound of Formula 1 for use as medication in treatment of eye diseases. In some embodiments the compound of Formula 1 formulations are useful for treatment of dry eye syndrome or more specifically for the treatment of dry eye secondary to presumed ocular surface inflammation.

In some embodiments the invention provides formulations of the compound of Formula 1 for topical administration to the eye. In some aspects the formulations are aqueous solutions of the compound of Formula 1. In some embodiments, the formulations of the compound of Formula 1 also contain other pharmaceutically acceptable ingredients. In some aspects the pharmaceutically acceptable ingredients is an ingredient that improves the stability of the compound of Formula 1 in formulations. In some aspects the ingredient used to increase the stability of the compound of Formula 1 is one or more antioxidant. In some cases the aqueous solution of the compound of Formula 1 is buffered to a pH of about 6.0-8.0 to further increase the stability of the compound of Formula 1. In some aspects the formulation is additionally sparged with an inert gas to further increase the stability of the compound of Formula 1.

Polymorphs, Salts, and Formulations

The compositions of the invention may comprise the amorphous form of the compound of Formula 1 or any of its crystalline forms I, II, III, IV, V, or VI or a combination thereof. In some embodiments of the invention the amorphous form of the compound of Formula 1 is used to prepare the formulation. In some embodiments a crystalline form of the compound of Formula 1 is used in the formulations. In some embodiments the compound of Formula 1 used is the crystalline form I, or II, or III, or IV, or V, or VI. In some embodiments the amorphous form of the compound of Formula 1 is used in combination with one or more of the crystalline forms I, II, III, IV, V or VI. In some embodiments the form I of the compound of Formula 1 is used in combination with one or more of the amorphous form, form II, form III, form IV, form V or form VI. In some embodiments the form II of the compound of Formula 1 is used in combination with one or more of the amorphous form, form I, form III, form IV, form V or form VI. In some embodiments the form III of the compound of Formula 1 is used in combination with one or more of the amorphous form, form I, form II, form IV, form V or form VI. In some embodiments the form IV of the compound of Formula 1 is used in combination with one or more of the amorphous form, form I, form II, form III, form V or form VI. In some embodiments the form V of the compound of Formula 1 is used in combination with one or more of the amorphous form, form I, form II, form III, form IV or form VI. In some embodiments the form VI of the compound of Formula 1 is used in combination with one or more of the amorphous form, form I, form II, form III, form IV or form V.

In some embodiments of the invention, addition of sodium bicarbonate is made to the amorphous form or any of crystalline forms I, II, III, IV, V or VI, or a mixture thereof of the compound of Formula 1 to convert it to a sodium salt. In some embodiments of the invention, the amorphous form or any of the crystalline forms I, II, III, IV, V or VI are formulated as their sodium, potassium, lithium, magnesium, zinc, or calcium salts.

It is envisioned additionally, that the amorphous form or any of the crystalline forms of the compound of Formula 1, or a combination thereof, may be attached releasably to biocompatible polymers for use in sustained release formulations on, in or attached to inserts for topical, intraocular, periocular, or systemic administration. The controlled release from a biocompatible polymer may be utilized with a water soluble polymer to form an instillable formulation, as well. The controlled release from a biocompatible polymer, such as for example, PLGA microspheres or nanospheres, may be utilized in a formulation suitable for intra ocular implantation or injection for sustained release administration, as well. Any suitable biodegradable and biocompatible polymer may be used.

Additionally, the amorphous form or any of the crystalline Forms I, II, III, IV, V, and VI, or combinations thereof, of the compound of Formula 1 may be suitable for use in sustained release formulations where the drug entity may remain as a solid. Further, the calcium salt of the free acid of any of these forms is envisioned to be useful in slow release formulations, as a solid formulation, gel formulation or liquid formulation.

Solutions

The present invention provides stable pharmaceutical compositions of the compound of Formula 1 for treatment of diseases, such as eye diseases. In some aspects, the current invention provides compositions and methods for stabilizing liquid formulations of the compound of Formula 1. In some embodiments, the liquid formulations of the compound of Formula 1 are prepared by dissolving the amorphous form or any of the crystalline forms of the compound of Formula 1, or a combination thereof, in sterile aqueous solution. In some embodiments the aqueous solution is a physiological saline or a buffer solution.

Other vehicles may be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The amount of the compound of Formula 1 in the formulations of the invention may range in concentration from about 0.0001% to 10.0 w/v %, about 0.005% to 10.0 w/v %, about 0.01% to 10.0 w/v %, about 0.05% to 10.0 w/v %, about 0.1% to 10.0 w/v %, about 0.5% to 10.0 w/v %, about 1.0% to 10.0 w/v %, about 2.0% to 10.0 w/v %, about 3.0% to 10.0 w/v %, about 4.0% to 10.0 w/v %, or about 5.0% to 10.0 w/v %, 6.0% to 10.0 w/v %, about 7.0% to 10.0 w/v %, about 8.0% to 10.0 w/v %, or about 9.0% to 10.0 w/v %. In some embodiments, the amount of the compound of Formula 1 is in the range of about 1% to about 20.0 w/v %, about 5% to about 20.0 w/v %, about 7% to about 20.0 w/v %, about 10% to about 20.0 w/v %, about 12% to about 20.0 w/v %, about 15% to about 20.0 w/v %, or about 17% to about 20.0 w/v %; about 5% to about 25.0 w/v %, about 7% to about 25.0 w/v %, about 10% to about 25.0 w/v %, about 12% to about 25.0 w/v %, about 15% to about 25.0 w/v %, about 17% to about 25.0 w/v %, about 20% to about 25.0 w/v %, or about 22% to about 25.0 w/v %; about 5% to about 35.0 w/v %, about 7% to about 35.0 w/v %, about 10% to about 35.0 w/v %, about 12% to about 35.0 w/v %, about 15% to about 35.0 w/v %, about 17% to about 35.0 w/v %, about 20% to about 35.0 w/v %, 22% to about 35.0 w/v %, 25% to about 35.0 w/v %, 27% to about 35.0 w/v %, 30% to about 35.0 w/v %, or about 32% to about 35.0 w/v %; about 5% to about 40.0 w/v %, about 7% to about 40.0 w/v %, about 10% to about 40.0 w/v %, about 12% to about 40.0 w/v %, about 15% to about 40.0 w/v %, about 17% to about 40.0 w/v %, about 20% to about 40.0 w/v %, 22% to about 40.0 w/v %, 25% to about 40.0 w/v %, 27% to about 40.0 w/v %, w/v %, 30% to about 40.0 w/v %, 33% to about 40.0 w/v %, 35% to about 40.0 w/v %, or about 37% to about 40.0 w/v %; about 5% to about 50.0 w/v %, about 10% to about 50.0 w/v %, about 12% to about 50.0 w/v %, about 15% to about 50.0 w/v %, about 20% to about 50.0 w/v %, about 22% to about 50.0 w/v %, about 25% to about 50.0 w/v %, about 27% to about 50.0 w/v %, about 30% to about 50.0 w/v %, about 32% to about 50.0 w/v %, about 35% to about 50.0 w/v %, about 37% to about 50.0 w/v %, about 40% to about 50.0 w/v %, about 42% to about 50.0 w/v %, about 45% to about 50.0 w/v %, or about 47% to about 50.0 w/v %.

In some embodiments, the amount of compound of Formula 1 is about 0.5%, about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5, about 10%, about 15%, about 20%, about 25%, about 30%, about 35%, about 40%, about 45%, or about 50% w/v.

One embodiment of the invention has a formulation of about 1.0% to 10.0 w/v % of the compound of Formula 1. One embodiment of the invention has a formulation of about 0.01% to 10.0 w/v % of the compound of Formula 1. One embodiment of the invention has a formulation of about 5.0% to 10.0 w/v % of the compound of Formula 1. One embodiment of the invention has a formulation of about 10% to about 50.0 w/v % of the compound of Formula 1. One embodiment of the invention has a formulation of about 10% to about 20.0 w/v % of the compound of Formula 1. One embodiment of the invention has a formulation of about 10% to about 35.0 w/v % of the compound of Formula 1.

In some embodiments in order to increase the stability of the compound of Formula 1, the formulations are buffered by addition of a buffer component. In some embodiments the aqueous solution is buffered to a pH of about 6.0 to about 8.0. In some embodiments the pH of the aqueous solution is buffered to a range of about 6.5 to about 8.0, about 7.0 to about 8.0, about 7.5 to about 8.0, about 6.0 to about 7.5, about 6.5 to about 7.5, about 7.0 to about 7.5, 6.0 to about 7.0, about 6.5 to about 7.0, about 7.0 to about 7.5, or about 7.5 to about 8.0. In some embodiments the aqueous solution is buffered to a pH of about 6.0, about 6.5, about 7.0, about 7.5, about 8.0 or about 8.5

In some embodiments the aqueous solution is buffered to a pH of about 6.0 to about 8.0 with Sodium Phosphate, Monobasic. In some embodiments the pH of the aqueous solution is buffered to a range of about 6.5 to about 8.0, about 7.0 to about 8.0, about 7.5 to about 8.0, about 6.0 to about 7.5, about 6.5 to about 7.5, about 7.0 to about 7.5, 6.0 to about 7.0, about 6.5 to about 7.0, about 7.0 to about 7.5, or about 7.5 to about 8.0. In some embodiments the aqueous solution is buffered to a pH of about 6.0, about 6.5, about 7.0, about 7.5, about 8.0 or about 8.5 with Sodium Phosphate, Monobasic. In some embodiments, the buffer is sodium phosphate dibasic.

Antioxidants

In some embodiments of the invention the formulations of the compound of Formula 1 contain one or more antioxidant to prevent oxidative degradation of the compound of Formula 1. In some embodiments the one or more antioxidants comprise a thiosulfate salt. In some embodiments the one or more antioxidants used in the formulation of the compound of Formula 1 include sodium thiosulfate. In some embodiments the antioxidants used in the formulation of the compound of Formula 1 include a metabisulfite salt. In some embodiments the antioxidants comprise sodium bisulfate.

Other anti-oxidants which can be used to form pharmaceutical formulations the invention include, but are not limited to, propyl, octyl and dodecyl esters of gallic acid, butylated hydroxyanisole (BHA, usually purchased as a mixture of ortho and meta isomers), green tea extract, uric acid, cysteine, pyruvate, nordihydroguaiaretic acid, ascorbic acid, salts of ascorbic acid such as ascorbyl palmitate and sodium ascorbate, ascorbyl glucosamine, vitamin E (i.e., tocopherols such as a-tocopherol), derivatives of vitamin E (e.g., tocopheryl acetate), retinoids such as retinoic acid, retinol, trans-retinol, cis-retinol, mixtures of trans-retinol and cis-retinol, 3-dehydroretinol and derivatives of vitamin A (e.g., retinyl acetate, retinal and retinyl palmitate, also known as tetinyl palmitate), sodium citrate, sodium sulfite, lycopene, anthocyanids, bioflavinoids (e.g., hesperitin, naringen, rutin and quercetin), superoxide dismutase, glutathione peroxidase, butylated hydroxytoluene (BHT), indole-3-carbinol, pycnogenol, melatonin, sulforaphane, pregnenolone, lipoic acid and 4-hydroxy-5-methyl-3[2H]-furanone. In various embodiments, one or more of the above antioxidants are excluded, or are present in less than effective amounts, either alone or in combination.

In some embodiments the amount of antioxidants used is in the range of about 0.01-0.5% w/v. In some embodiments the amount of antioxidants used is in the range of about 0.1-about 0.5%, about 0.2-about 0.5%, about 0.3-about 0.5%, about 0.4-about 0.5%, about 0.01-about 0.4%, about 0.1-about 0.4%, about 0.2-about 0.4%, about 0.3-about 0.4%, about 0.01-about 0.3%, about 0.1-about 0.3%, about 0.2-about 0.3%, about 0.01-about 0.2%, about 0.1-about 0.2%, or about 0.01-about 0.1%. In some embodiments, sodium thiosulfate is present in an amount to provide antioxidant stability to the formulation, and the amount of sodium thiosulfate as a percentage by weight of all total antioxidants is greater than 50% by weight.

Sparging

In some embodiments the stability of the compound of Formula 1 in formulations is further improved by sparging the formulation with an inert gas. A variety of inert gases may be used as a sparging material including but not limited to nitrogen, argon, and helium. In some embodiments the inert gas is nitrogen. The sparging is generally carried out till the oxygen is reduced or completely removed from the formulations of the compound of Formula. 1, The time period for sparging depends in several factors including the amount of formulation, the effectiveness of agitation and the flow rate of the inert gas. In some embodiments, sparging is done by bubbling the inert gas through the formulations for a period of about 1 min-about 12 h. In some embodiments the formulations are sparged for a period of about 1 min-about 11 h, about 1 min-about 10 h, about 1 min-about 9 h, about 1 min-about 8 h, about 1 min-about 7 h, about 1 min about 6 h, about 1 min-about 5 h, about 1 min-about 4 h, about 1 min-about 3 h, about 1 min-about 2 h, about 1 min-about 1 h, about 1 min about 45 min, about 1 min-about 30 min, about 1 min-about 15 min, about 1 min-about 10 min, about 1 min-about 9 min, about 1 min-about 8 min, about 1 min-about 7 min, about 1 min-about 6 min, about 1 min-about 5 min, about 1 min-about 4 min, about 1 min-about 3 min, about 1 min-about 2 min. In some embodiments, sparging is performed for less than about 1 minute.

Additional Excipients and Components

The solubility of the components of the present compositions may be enhanced by a surfactant or other appropriate co-solvent in the composition. Such cosolvents include polysorbate 20, 60, and 80, Pluronic® F68, F-84 and P-103, cyclodextrin, or other agents known to those skilled in the art. Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed. The surfactant may be any suitable, non-toxic compound that is non-reactive with the medicament and that substantially reduces the surface tension between the medicament, the excipient and the site of administration.

In some embodiments the formulations of the invention contain no surfactants. In some embodiments, the formulations of the invention are topical formulations containing no surfactants. In some further embodiments the formulations contain substantially no surfactant, i.e. contain less than approximately 0.0001% by weight of surface-active agents. In some embodiments, the formulations contain essentially no surfactants.

If desired, however, the formulations can contain surface-active agents conventionally employed in topical formulations, such as oleic acid, lecithin, sorbitan trioleate, cetylpyridinium chloride, benzalkonium chloride, polyoxyethylene (20) sorbitan monolaurate, polyoxyethylene (20) sorbitan monostearate, polyoxyethylene (20) sorbitan monooleate, polyoxypropylene/polyoxyethylene block copolymers, polyoxypropylene/polyoxyethylene/ethylene diamine block copolymers, ethoxylated castor oil and the like, where the proportion of surface-active agents, if present, can be about 0.0001 to 1% by weight, or about 0.001 to 0.1% by weight, based on the total formulation. Other suitable surfactant/emulsifying agents would be known to one of skill in the art and are listed in the CTFA International Cosmetic Ingredient Dictionary and Handbook, Vol. 2, 7 th Edition (1997).

Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate. In some embodiments, the formulations of the current invention contain no or essentially no suspending agents. In some further embodiments, the formulations are solutions containing no suspending agents.

Chelating agents which can be used to form pharmaceutical compositions and dosage forms of the invention include, but are not limited to, ethylene diaminetetraacetic acid (EDTA), EDTA disodium, calcium disodium edetate, EDTA trisodium, albumin, transferrin, desferoxamine, desferal, desferoxamine mesylate, EDTA tetrasodium and EDTA dipotassium, sodium metasilicate or combinations of any of these.

Preservatives which can be used to form pharmaceutical compositions and dosage forms of the invention include, but are not limited to, purite, peroxides, perborates, imidazolidinyl urea, diazolidinyl urea, phenoxyethanol, alkonium chlorides including benzalkonium chlorides, methylparaben, ethylparaben and propylparaben. In other embodiments, suitable preservatives for the compositions of the invention include: benzalkonium chloride, purite, peroxides, perborates, thimerosal, chlorobutanol, methyl paraben, propyl paraben, phenylethyl alcohol, edetate disodium, sorbic acid, Onamer M, or other agents known to those skilled in the art. In some embodiments of the invention, such preservatives may be employed at a level of from 0.004% to 0.02% w/v. In some compositions of the present application the preservative, for example, benzalkonium chloride, methyl paraben, and/or propyl paraben, may be employed at a level of from about 0.001% to less than about 0.01%, e.g. from about 0.001% to about 0.008%, or about 0.005% w/v. It has been found that a concentration of benzalkonium chloride of about 0.005% may be sufficient to preserve the compositions of the present invention from microbial attack. For example, ophthalmic drops or formulations for application to skin may use a mixture of methyl and propyl parabens at about 0.02% w/v and about 0.04% w/v respectively. In some embodiments, these formulations use methyl paraben and/or propyl paraben in amounts up to about 0.02% w/v and up to about 0.04% w/v respectively, which encompasses the embodiments where no methyl paraben or no propyl paraben is used. In various embodiments, preservatives are essentially excluded.

Preservatives may be preferred to prevent microbial contamination during use. Suitable preservatives include: benzalkonium chloride, thimerosal, chlorobutanol, methyl paraben, ethyl paraben, propyl paraben, phenylethyl alcohol, imidazolidinyl urea, diazolidinyl urea, phenoxyethanol, edetate disodium, sorbic acid, Onamer M, or other agents known to those skilled in the art. In the prior art ophthalmic products, such preservatives may be employed at a level of from 0.004% to 0.02%.

In some of the compositions of the present application, methyl paraben and propyl paraben are used in combination.

In the compositions of the present application the preservative benzalkonium chloride, may be employed at a level of from about 0.001% to less than about 0.01%, e.g. from about 0.001% to about 0.008%, or about 0.005% by weight.

Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, purite, peroxides, perborates and combinations thereof.

In some embodiments, the formulations of the invention include one or more lubricants. Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition. In some embodiments, the formulations contain no or essentially no lubricants. In some further embodiments, the formulations are solutions containing no lubricating agents.

The formulations of the invention include one or more thickening agents. Thickening agents which can be used to form pharmaceutical compositions and dosage forms of the invention include, but are not limited to, isopropyl myristate, isopropyl palmitate, isodecyl neopentanoate, squalene, mineral oil, $C_{12}$-$C_{15}$ benzoate and hydrogenated polyisobutene. Agents which would not disrupt other compounds of the final product may be desirable, such as non-ionic thickening agents. The selection of additional thickening agents is well within the skill of one in the art. In some embodiments the formulations contain essentially no thickening agents. In some cases the formulations contain no thickening agents. In some embodiments the formulations are solution containing no thickening agents.

The formulations of the invention can further include other pharmacological active ingredients as far as they do not contradict the purpose of the present invention. In a combination of plural active ingredients, their respective contents may be suitably increased or decreased in consideration of their effects and safety.

Stability and Degradation

In some embodiments, the total the compound of Formula 1 degradation products formed in the formulations of the present invention is less than 1.0% when stored at a temperature of 40° C. for a period of one month. In some further embodiments, the total degradation products of the compound of Formula 1 formed is less than about 0.9%, about 0.8%, about 0.7%, about 0.6%, about 0.5%, about 0.4%, about 0.3%, about 0.2%, or about 0.1% when stored at a temperature of 40° C. for a period of one month.

In some further embodiments, the total degradation products of the compound of Formula 1 formed in the formulations of the present invention is less than 1.0% when stored at a temperature of 40° C. for a period of about two months, about three months, about four months, about five months about six months.

In some cases the pharmaceutically acceptable formulation expires in about 1-5 years. In some cases the formulation expires in about 1, 2, 3 or 4 years. In some cases the formulation expires in more than 5 years. In some cases the formulation expires in less than a year. In some cases the formulation expires in 1, 2, 3, 4, 5, 6, 7, 8, 9, 10, or 11 months.

In some cases the total the compound of Formula 1 degradation products at the time of product expiration are in the range of above 0.1-10%. In some cases the total degradation product at the time of expiration is in the range of about 0.01-1, about 0.01-2, about 0.01-3, about 0.01-4, about 0.01-5, about 0.01-6, about 0.01-7, about 0.01-8, or about 0.01-9, about 1-2, about 1-3, about 1-4, about 1-5, about 1-6, about 1-7, about 1-8, about 1-9, about 2-3, about 3-4, about 2-5, about 2-6, about 2-7, about 2-8, about 2-9, about 3-4, about 3-5, about 3-6, about 3-7, about 3-8, about 3-9, about 3-10, about 4-5, about 4-6, about 4-7, about 4-8, about 4-9, about 4-10, about 5-6, about 5-7, about 5-8, about 5-9, about 5-10, about 6-7, about 6-8, about 6-9, about 6-10, about 7-8, about 7-9, about 7-10, about 8-9, about 8-10 or about 9-10%. In some embodiments the amount of total degradation product at the time of expiration is about 1%, about 2%, about 3%, about 4%, about 5%, about 6%, about 7%, about 8%, about 9%, about 10%. In some embodiments the amount of total degradation product at the time of expiration is about 0.01%, about 0.05%, about 0.1%, about 0.15%, about 0.2%, about 0.25%, about 0.3%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, or about 1.0%.

In some cases pharmaceutical formulations of the compound of Formula 1 are stored at −5 to 65° C. In some cases the formulations can be stored at about 0° C., about 5° C., about 10° C., about 15° C., about 20° C., about 25° C., about 30° C., about 35° C., about 40° C., about 45° C., about 50° C., about 55° C., about 60° C., or about 65° C. In various embodiments, the compositions are stored at or below ambient temperature.

II. Methods of Treatment

In some embodiments, the compound of Formula 1 is present in an amount sufficient to exert a therapeutic effect to reduce symptoms of dry eye by an average of at least about 5, 10, 15, 20, 25, 30, 40, 50, 60, 70, 80, 90, more than 90%, or substantially eliminate symptoms of dry eye.

In some embodiments, the compound of Formula I is present in an amount sufficient to decrease retinal neovascularization in a treated eye of a subject by an average of at least about 5, 10, 15, 20, 25, 30, 40, 50, 60, 70, 80, 90, more than 90%, or substantially eliminate retinal neovascularization.

In some embodiments, an effective amount of the compound of Formula 1 is a daily dose of about $1\times10^{-10}$, $1\times10^{-9}$, $1\times10^{-8}$, $1\times10^{-7}$, $1\times10^{-6}$, $1\times10^{-5}$, $\times10^{-4}$, $1\times10^{-3}$, $1\times10^{-2}$, $1\times10^{-1}$, 1, $1\times10^{1}$, $1\times10^{2}$ grams.

Administration

The formulations of the present invention may draw upon many suitable modes of administration. Delivery to affected regions of the body may be achieved either via local or systemic administration. Suitable formulations and additional carriers are described in Remington "The Science and Practice of Pharmacy" ($20^{th}$ Ed., Lippincott Williams &

Wilkins, Baltimore Md.), the teachings of which are incorporated by reference in their entirety herein.

In order to reduce inflammation in eye disorders, the pharmaceutical composition of the invention is preferably delivered to the retina, intraocular space, ocular surface, interconnecting innervation, conjunctiva, lacrimal glands, or meibomian glands.

In some embodiments, the therapeutic agent is administered topically. In some embodiments, the therapeutic agent is administered topically, via an eye drop. If combinations of agents are administered as separate compositions, they may be administered by the same route or by different routes. If combinations of agents are administered in a single composition, they may be administered by any suitable route. In some embodiments, the combinations of agent are administered as a single composition topically. In various embodiments, an effective amount of the therapeutic agent is administered to the surface of the eye without administration of an effective amount of therapeutic agent to the skin.

In some embodiments, the compound of Formula 1 is administered in a single dose. A single dose of the compound of Formula 1 may also be used when it is co-administered with another substance (e.g., an analgesic) for treatment of an acute condition.

In some embodiments, the compound of Formula 1 (by itself or in combination with other drugs) is administered in multiple doses. Dosing may be about once, twice, three times, four times, five times, six times, seven times, eight times, nine times, ten times or more than ten times per day. Dosing may be about once a year, twice a year, every six months, every 4 months, every 3 months, every 60 days, once a month, once every two weeks, once a week, or once every other day. In one embodiment the drug is an analgesic. In another embodiment the compound of Formula 1 and another therapeutic substance are administered together about once per day to about 10 times per day. In another embodiment the administration of the compound of Formula 1 and another therapeutic substance continues for less than about 7 days. In yet another embodiment the co-administration continues for more than about 6, 10, 14, 28 days, two months, six months, or one year. In some cases, co-administered dosing is maintained as long as necessary, e.g., dosing for chronic inflammation.

Administration of the compositions of the invention may continue as long as necessary. In some embodiments, a composition of the invention is administered for more than 1, 2, 3, 4, 5, 6, 7, 14, or 28 days. In some embodiments, a composition of the invention is administered for less than 28, 14, 7, 6, 5, 4, 3, 2, or 1 day. In some embodiments, a composition of the invention is administered chronically on an ongoing basis, e.g., for the treatment of chronic pain.

Dosing for the compound of Formula 1 formulations of the invention may be found by routine experimentation. The daily dose can range from about $1\times10^{-8}$ g to 5000 mg. Daily dose range may depend on the form of the compound of Formula 1 e.g., the esters or salts used, and/or route of administration, as described herein. For example, for systemic administration, typical daily dose ranges are, e.g. about 1-5000 mg, or about 1-3000 mg, or about 1-2000 mg, or about 1-1000 mg, or about 1-500 mg, or about 1-100 mg, or about 10-5000 mg, or about 10-3000 mg, or about 10-2000 mg, or about 10-1000 mg, or about 10-500 mg, or about 10-200 mg, or about 10-100 mg, or about 20-2000 mg or about 20-1500 mg or about 20-1000 mg or about 20-500 mg, or about 20-100 mg, or about 50-5000 mg, or about 50-4000 mg, or about 50-3000 mg, or about 50-2000 mg, or about 50-1000 mg, or about 50-500 mg, or about 50-100 mg, about 100-5000 mg, or about 100-4000 mg, or about 100-3000 mg, or about 100-2000 mg, or about 100-1000 mg, or about 100-500 mg. In some embodiments, the daily dose of the compound of Formula 1 is about 100, 200, 300, 400, 500, 600, 700, 800, 900, or 1000 mg. In some embodiments, the daily dose of the compound of Formula 1 is 10 mg. In some embodiments, the daily dose of the compound of Formula 1 is 100 mg. In some embodiments, the daily dose of the compound of Formula 1 is 500 mg. In some embodiments, the daily dose of the compound of Formula 1 is 1000 mg.

For topical delivery to the ocular surface, the typical daily dose ranges are, e.g. about $1\times10^{-8}$ g to 5.0 g, or about $1\times10^{-8}$ g to 2.5 g, or about $1\times10^{-8}$ g to 1.00 g, or about $1\times10^{-8}$ g to 0.5 g, or about $1\times10^{-8}$ g to 0.25 g, or about $1\times10^{-8}$ g to 0.1 g, or about $1\times10^{-8}$ g to 0.05 g, or about $1\times10^{-8}$ g to 0.025 g, or about $1\times10^{-8}$ g to $1\times10^{-2}$ g, or about $1\times10^{-8}$ g to $5\times10^{-3}$ g, or about $1\times10^{-8}$ g to $2.5\times10^{-3}$ g, or about $1\times10^{-8}$ g to $1\times10^{-3}$ g, or about $1\times10^{-8}$ g to $5\times10^{4}$ g, or about $1\times10^{-7}$ g to 5.0 g, or about $1\times10^{-7}$ g to 2.5 g, or about $1\times10^{-7}$ g to 1.00 g, or about $1\times10^{-7}$ g to 0.5 g, or about $1\times10^{-7}$ g to 0.25 g, or about $1\times10^{-7}$ g to 0.1 g, or about $1\times10^{-7}$ g to 0.05 g, or about $1\times10^{-7}$ g to 0.025 g, or about $1\times10^{-7}$ g to $1\times10^{-2}$ g, or about $1\times10^{-7}$ g to $5\times10^{-3}$ g, or about $1\times10^{-7}$ g to $2.5\times10^{-3}$ g, or about $1\times10^{-7}$ g to $1\times10^{-3}$ g, or about $1\times10^{-7}$ g to $5\times10^{4}$ g, or about $1\times10^{-6}$ g to 5.0 g, or about $1\times10^{-6}$ g to 2.5 g, or about $1\times10^{-6}$ g to 1 g, or about $1\times10^{-6}$ g to 0.5 g, or about $1\times10^{-6}$ g to 0.25 g, or about $1\times10^{-6}$ g to 0.1 g, or about $1\times10^{-6}$ g to $5\times10^{-2}$ g, or about $1\times10^{-6}$ g to $2.5\times10^{-2}$ g, or about $1\times10^{-6}$ g to $1\times10^{-2}$ g, or about $1\times10^{-6}$ g to $5\times10^{-3}$ g, or about $1\times10^{-6}$ g to $2.5\times10^{-3}$ g, or about $1\times10^{-6}$ g to $1\times10^{-3}$ g, or about $1\times10^{-6}$ g to $5\times10^{4}$ g, or about $1\times10^{-5}$ g to 5 g, or about $1\times10^{-5}$ g to 2.5 g, or about $1\times10^{-5}$ g to 1 g, or about $1\times10^{-5}$ g to 0.5 g, or about $1\times10^{-5}$ g to 0.25 g, or about $1\times10^{-5}$ g to 0.1 g, or about $1\times10^{-5}$ g to 0.05 g, or about $1\times10^{-5}$ g to $2.5\times10^{-2}$ g, or about $1\times10^{-5}$ g to $1\times10^{-2}$ g, or about $1\times10^{-5}$ g to $5\times10^{-3}$ g, or about $1\times10^{-5}$ g to $2.5\times10^{-3}$ g, or about $1\times10^{-5}$ g to $1\times10^{-3}$ g, or about $1\times10^{-5}$ g to $5\times10^{4}$ g. In some embodiments, the daily dose of the compound of Formula 1 is about $1\times10^{-7}$, $1\times10^{-6}$, $1\times10^{-5}$, $1\times10^{-4}$, $1\times10^{-3}$ g, $1\times10^{-2}$ g, $1\times10^{1}$ g, or 1 g. In some embodiments, the daily dose of the compound of Formula 1 is $1\times10^{-7}$ g. In some embodiments, the daily dose of the compound of Formula 1 is $1\times10^{-5}$ g. In some embodiments, the daily dose of the compound of Formula 1 is $1\times10^{-3}$ g. In some embodiments, the daily dose of the compound of Formula 1 is $1\times10^{-2}$ g. In some embodiments the subject dose ranges from about $1\times10^{-8}$ g to 5.0 g, or about $1\times10^{-8}$ g to 2.5 g, or about $1\times10^{-8}$ g to 1.00 g, or about $1\times10^{-8}$ g to 0.5 g, or about $1\times10^{-8}$ g to 0.25 g, or about $1\times10^{-8}$ g to 0.1 g, or about $1\times10^{-8}$ g to 0.05 g, or about $1\times10^{-8}$ g to 0.025 g, or about $1\times10^{-8}$ g to $1\times10^{-2}$ g, or about $1\times10^{-8}$ g to $5\times10^{-3}$ g, or about $1\times10^{-8}$ g to $2.5\times10^{-3}$ g, or about $1\times10^{-8}$ g to $1\times10^{-3}$ g, or about $1\times10^{-8}$ g to $5\times10^{-4}$ g, or about $1\times10^{-7}$ g to 5.0 g, or about $1\times10^{-7}$ g to 2.5 g, or about $1\times10^{-7}$ g to 1.00 g, or about $1\times10^{-7}$ g to 0.5 g, or about $1\times10^{-7}$ g to 0.25 g, or about $1\times10^{-7}$ g to 0.1 g, or about $1\times10^{-7}$ g to 0.05 g, or about $1\times10^{-7}$ g to 0.025 g, or about $1\times10^{-7}$ g to $1\times10^{-2}$ g, or about $1\times10^{-7}$ g to $5\times10^{-3}$ g, or about $1\times10^{-7}$ g to $2.5\times10^{-3}$ g, or about $1\times10^{-7}$ g to $1\times10^{-3}$ g, or about $1\times10^{-7}$ g to $5\times10^{-4}$ g, or about $1\times10^{-6}$ g to 5.0 g, or about $1\times10^{-6}$ g to 2.5 g, or about $1\times10^{-6}$ g to 1 g, or about $1\times10^{-6}$ g to 0.5 g, or about $1\times10^{-6}$ g to 0.25 g, or about $1\times10^{-6}$ g to 0.1 g, or about $1\times10^{-6}$ g to $5\times10^{-2}$ g, or about $1\times10^{-6}$ g to $5\times10^{-2}$ g, or about $1\times10^{-6}$ g to $1\times10^{-2}$ g, or about $1\times10^{-6}$ g to $5\times10^{-3}$ g, or about $1\times10^{-6}$ g to $2.5\times10^{-3}$ g, or about $1\times10^{-6}$ g to $1\times10^{-3}$ g, or about $1\times10^{-6}$ g to $5\times10^{-4}$ g, or about $1\times10^{-5}$ g to 5 g, or about $1\times10^{-5}$ g to 2.5 g, or about $1\times10^{-5}$ g to 1 g, or about $1\times10^{-5}$ g to 0.5 g, or about $1\times10^{-5}$ g to 0.25 g, or about $1\times10^{-5}$ g to 0.1 g, or about $1\times10^{-5}$ g to 0.05 g, or about $1\times10^{-5}$ g to $2.5\times10^{-2}$ g, or about $1\times10^{-5}$ g to $1\times10^{-2}$ g, or about $1\times10^{-5}$ g to $5\times10^{-3}$ g, or about $1\times10^{-5}$ g to $2.5\times10^{-3}$ g, or about $1\times10^{-5}$ g to $1\times10^{-3}$ g, or about $1\times10^{-5}$ g to $5\times10^{-4}$ g. In some embodiments, the individual dose as described above, is repeated 1, 2, 3, 4, 5, 6, 7, 8, 9, or 10 times per day.

In some embodiments of the invention, topical formulations of the invention release sufficient therapeutic agent intraocularly or periocularly to sustain a level of the compound of Formula 1 of at least about 10 nM, about 50 nM, about 100 nM, about 150 nM, about 200 nM, about 250 nM, about 300 nM, about 350 nM, about 500 nM, about 600 nM, about 700 nM, about 800 nM, about 900 nM, about 1 mM, about 2 mM, about 3 mM, about 5 mM, about 6 mM, about 7 mM, about 8 mM, about 9 mM, about 10 mM, about 15 mM, about 20 mM or about 25 mM from dose to dose.

In some embodiments of the invention, an eye drop formulation of the invention release sufficient therapeutic agent intraocularly or periocularly to achieve a level of the compound of Formula 1 in the retina of at least about 10 nM, about 50 nM, about 100 nM, about 150 nM, about 200 nM, about 250 nM, about 300 nM, about 350 nM, about 500 nM, about 600 nM, about 700 nM, about 800 nM, about 900 nM, about 1 mM, about 2 mM, about 3 mM, about 5 mM, about 6 mM, about 7 mM, about 8 mM, about 9 mM, about 10 mM, about 15 mM, about 20 mM or about 25 mM from dose to dose. In some further embodiments, the level of compound of Formula 1 in the retina achieved by the therapeutic agents released by the eye drop formulations of the current invention is less than about 10 nM. In some embodiments, the level of Formula 1 in the retina is less than about 9 nM, about 8 nM, about 7 nM, about 6 nM, about 5 nM, about 4 nM, about 3 nM, about 2 nM or about 1 nM. In some cases, essentially no amount of compound of Formula 1 from the eye drop formulations of the invention reaches the retina. In some cases, no amount of the compound of Formula 1 from the eye drop formulations of the invention reaches the retina. In some cases, the formulations of the invention can also be used for slow or sustained release intraocular or periocular devices and formulations. In some embodiments, a typical dose range is about 0.1 mg to about 100 mg of the compound of Formula 1 released over the dosing period. In other embodiments, about 1 mg to about 50 mg, about 1 to about 25 mg, about 5 mg to about 100 mg, about 5 to about 50 mg, about 5 to about 25 mg, about 10 mg to about 100 mg, about 10 mg to about 50 mg, about 10 mg to about 25 mg, or about 15 mg to about 50 mg is released over the dosing period. The dosing period for slow release intraocular or periocular devices and formulations, typically range from about 10 days to about 1 year, about 30 days to about 1 year, about 60 days to about 1 year, about 3 months to about 1 year, about 4 months to about 1 year, about 5 months to about 1 year, or about 6 months to about 1 year. In some embodiments, the slow release intraocular or periocular devices and formulations release therapeutic agent over the period of about 1 month to about 9 months, about 1 month to about 8 months, about 1 month to about 7 months, about 1 month, to about 6 months, about 1 month to about 5 months, about 1 month to about 4 months, or about 1 month to about 3 months. In other embodiments the slow release formulations and devices release therapeutic agent for up to 1 month, 2 months, 3 months, 4 months, 5 months, 6 months, 7 months, 8 months, 9 months, 10 months, 12 months, 18 months, 2 years, 30 months, or 3 years.

In some embodiments of the invention, the sustained release formulation or implantations release sufficient therapeutic agent intraocularly or periocularly to sustain a level of the compound of Formula 1 of at least about 10 nM, about 50 nM, about 100 nM, about 150 nM, about 200 nM, about 250 nM, about 300 nM, about 350 nM, about 500 nM, about 600 nM, about 700 nM, about 800 nM, about 900 nM, about 1 mM, about 2 mM, about 3 mM, about 5 mM, about 6 mM, about 7 mM, about 8 mM, about 9 mM, about 10 mM, about 15 mM, about 20 mM or about 25 mM across 1 year. In some embodiments of the invention, the sustained release formulation or implantations release sufficient therapeutic agent intraocularly or periocularly to sustain a level of the compound of Formula 1 of at least about 10 nM, about 50 nM, about 100 nM, about 150 nM, about 200 nM, about 250 nM, about 300 nM, about 350 nM, about 500 nM, about 600 nM, about 700 nM, about 800 nM, about 900 nM, about 1 mM, about 2 mM, about 3 mM, about 5 mM, about 6 mM, about 7 mM, about 8 mM, about 9 mM, about 10 mM, about 15 mM, about 20 mM or about 25 mM across 6 months.

The administration may be administered several times a day per eye, preferably one to ten times, more preferably one to four times, most preferably once a day. The size of the drop administered may be in the range of about 10-100 μl, about 10-90 μl, about 10-80 μl, about 10-70 μl, about 10-60 μl, about 10-50 μl, about 10-40 μl, about 10-30 μl, about 20-100 μl, about 20-90 μl, about 20-80 μl, about 20-70 μl, about 20-60 μl, about 20-50 μl, about 20-40 μl, or about 20-30 μl. One embodiment of the invention administers a drop in the range of about 10 to about 30 μl. One embodiment of the invention administers a drop in the range of about 10 to about 100 μl. One embodiment of the invention administers a drop in the range of about 20 to about 50 μl. One embodiment of the invention administers a drop in the range of about 20 to about 40 μl. One embodiment of the invention administers a drop in the range of about 10 to about 60 μl.

The formulations of the invention may be administered several drops per time, one to four drops, preferably one to three drops, more preferably one to two drops, and most preferably one drop per day. In one embodiment, the formulations of the invention are administered about one drop per time and one time per day.

The formulations of the invention may be packaged in multidose form or in single dose form. In some cases, the formulations are packaged in multidose forms. In some embodiments the formulations are packaged as single dose units. In some embodiments of the invention single dose packaging of the formulations can offer several advantages over multi dose packaging including dosage control, increased patient compliance, improved product labeling, and reduced counterfeiting. In various embodiments single dosage packaging of the formulations of the invention can be in form of vials, ampoules, tubes, bottles, pouches, packets, syringes or blister packs. In some embodiments the single dose containers can be grouped together and placed into additional containers. In some embodiments the secondary container is a pouch.

The formulations of the invention may be administered several drops per time, one to four drops one to three drops, one to two drops, or one drop per day.

III. Kits

The compositions of the current invention can also be provided as kits. The kits include a compound of the invention in suitable packaging, and written material that can include instructions for use, discussion of clinical studies, listing of side effects, and the like. The kit may further contain another therapeutic agent that is co-administered with the compound of Formula 1 of the invention. In some embodiments, the therapeutic agent and the compound of Formula 1 of the invention are provided as separate compositions in separate containers within the kit. In some embodiments, the therapeutic agent and the compound of Formula 1 of the invention are provided as a single composition within a container in the kit. Suitable packaging and additional articles for use (e.g., measuring cup for liquid preparations, foil wrapping to minimize exposure to air, dispensers, and the like) are known in the art and may be included in the kit.

EXAMPLES

Example 1

Stability of 5.0% Solution of the Compound of Formula 1

Three separate 5.0% aqueous solutions of the compound of Formula 1 were prepared and allowed to stand at temperatures of about 5° C., 25° C., and 40° C. respectively for a period of about 15 months. The percentage of total degradates was measured for each solution after about every 4 weeks. The results of this experiment are graphically represented in FIG. 1. The solution stored at 5° C., the aqueous solution of the compound of Formula 1 has about 5% of total degradation product after about 6 months (with no individual degradant above the ICH qualification threshold), while the solutions stored at 25° C. and 40° C. have 5% total degradation product in about 2 months (with no individual degradate above the ICH qualification threshold).

Example 2

Stability of Three Different Formulations of the Compound of Formula 1

Figure 2:
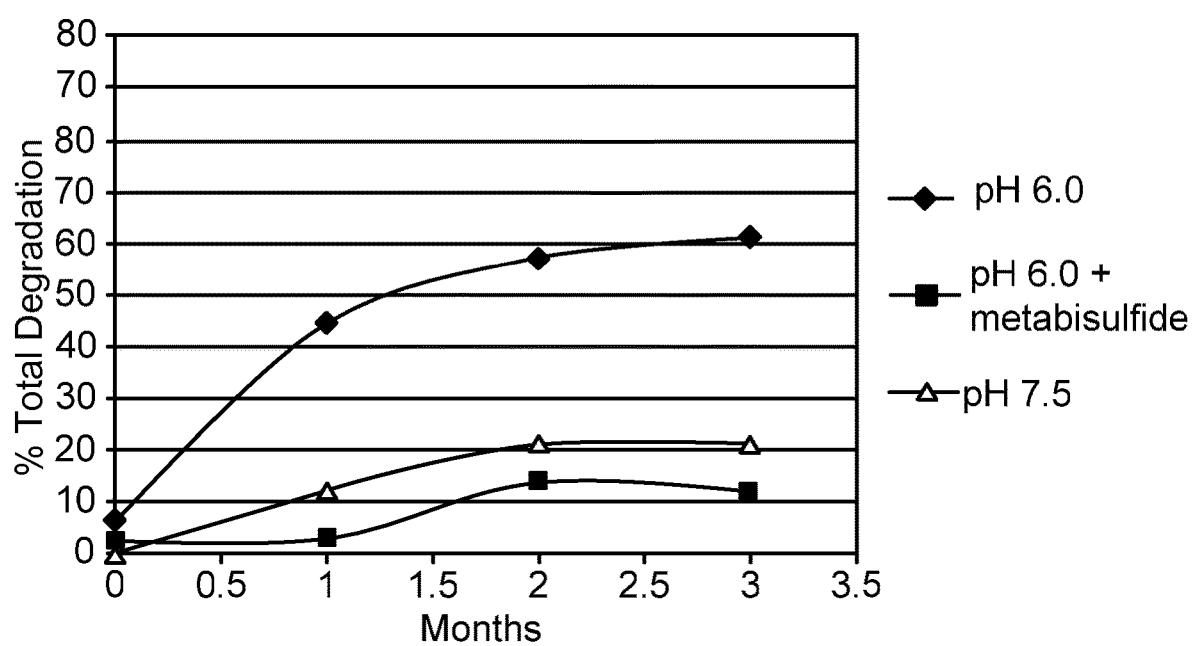
FIG. 2 shows the stability of the compound of Formula 1 in various formulations.

Three separate solutions of the compound of Formula 1 of same concentration were prepared. The first solution (pH=6.0) was stored at 40° C. without any further additives for about four months. The second solution (pH=6.0) was further treated with a metabisulfite salt and allowed to stand at 40° C. for about four months. The pH of the third solution was buffered to pH 7.5 and allowed to stand at 40° C. for about 4 months without any further additives. The percentage of total degradates was measured for each solution after about every 4 weeks. The results of this experiment are graphically represented in FIG. 2. Addition of antioxidant increases the stability of the formulations as did increasing the pH to about 7.5 without the addition of any antioxidants.

Example 3

Effect of Antioxidants on Stability

Figure 3:
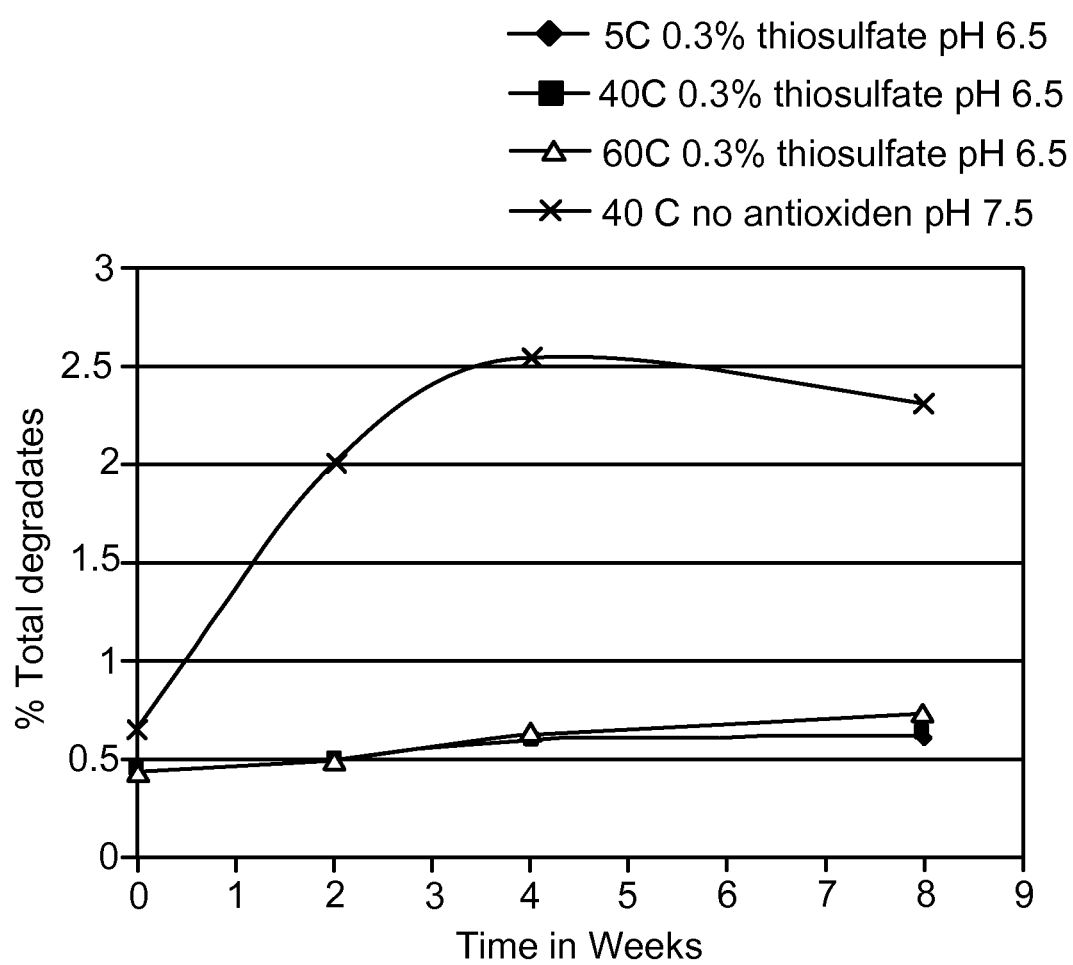
FIG. 3 shows the stability of the compound of Formula 1 in a 3% opthalmic solution in various conditions.

Four separate solutions containing 3% w/v of the compound of Formula 1 were prepared. The pH of the first solution was buffered to 6.5, 0.3% w/v thiosulfate salt was added and the solution was stored at 50° C. for about nine weeks. The pH of the second solution was adjusted to 6.5, 0.3% thiosulfate salt was added and the solution was stored at 40° C. for about nine weeks. The pH of the third solution was buffered to 6.5, 0.3% thiosulfate salt was added and the solution was allowed to stand at 60° C. for about nine months. No antioxidant was added to the fourth solution which was buffered to a pH of 7.5 and allowed to stand at a temperature of 40° C. for about 9 weeks. The percentage of total degradates was measured for each solution after about every 2-4 weeks. The results of this experiment are graphically represented in FIG. 3. Addition of antioxidant increased the stability of the formulations.

Example 4

Effect of Concentration of the Compound of Formula 1 on Formulation Stability

Figure 4:
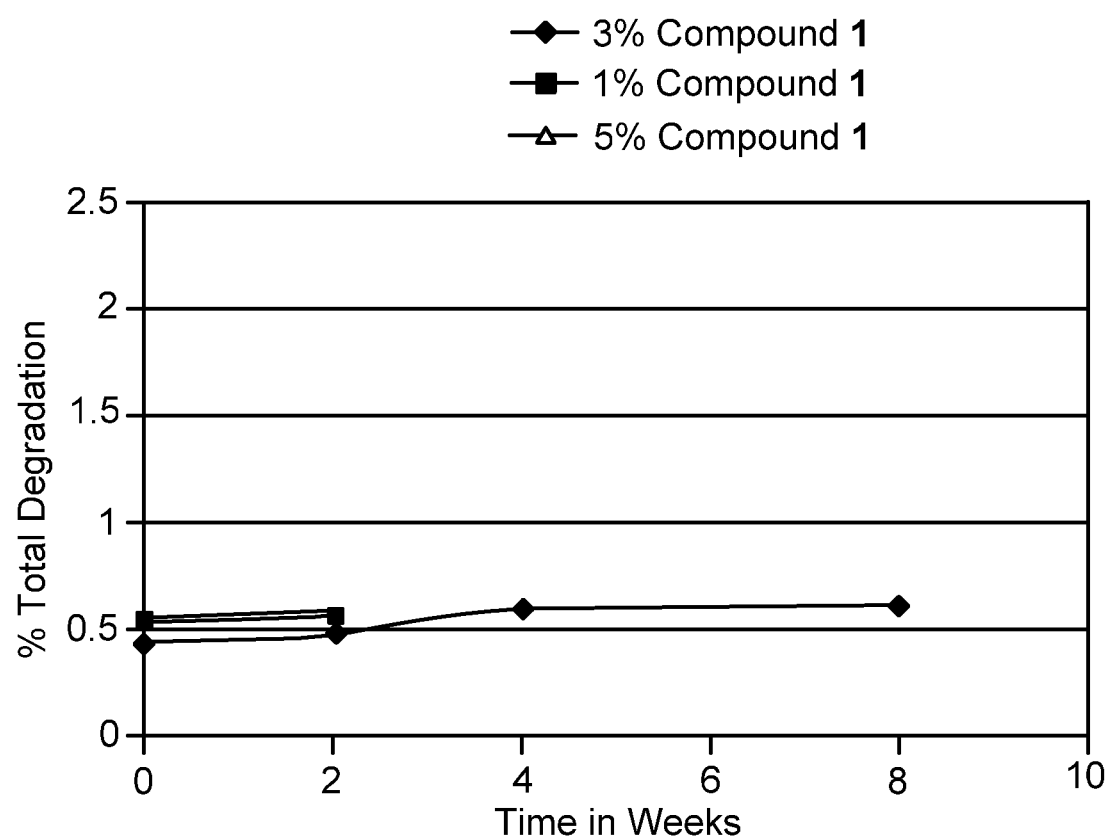
FIG. 4 shows the stability of the compound of Formula 1 in various concentrations by showing the % total degradation of the compound of Formula 1 over time upon storage at 40° C.

Three different concentrations of the compound of Formula 1, 1.0%, 3.0% and 5.0% were studied. The samples were monitored at a temperature of 40° C. The pH of the three solutions was maintained in the range of 7.0-7.5. The total % degradation of the three solutions was monitored with respect to time. The results of this experiment are graphically represented in FIG. 4. For the first two weeks, all three compositions had similar stability under similar conditions.

Solutions both with and without 0.1% EDTA were monitored. The presence or absence of EDTA did significantly change the stability of the formulations of the compound of Formula 1 in these experiments.

Example 5

Figure 5:
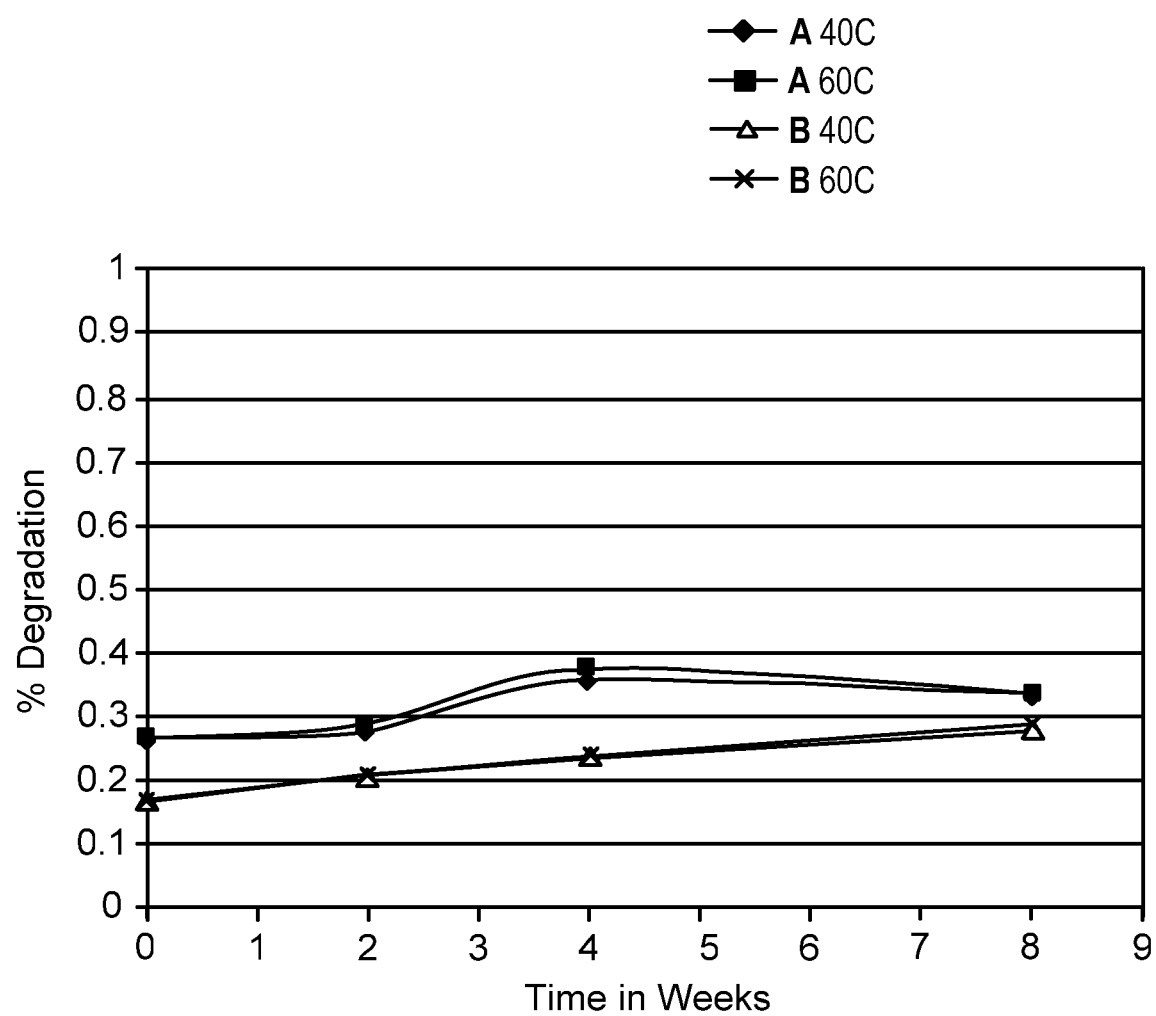
FIG. 5 shows the stability of the compound of Formula 1 by showing the appearance of degradation products A and B at various temperatures over time.

Study of the Stability of the Individual Degradates of the Compound of Formula 1 Over the Period of 8 Weeks Two solutions containing 5.0% w/v of the compound of Formula 1 were prepared. The first solution was stored at 40° C. for about 9 weeks and the second solution was stored at 60° C. for a period of about nine weeks. The percentage of each of the two major degradates of Formula 1 (degradate A and degradate B) was measured by HPLC analysis for each solution after about every 2-4 weeks. The results of this experiment are graphically represented in FIG. 5.

The storage temperature did not significantly affect the % formation of degradates A and B as both the solutions (one at 40° C. and the other at 60° C.) displayed comparable amount of individual degradates at any particular time.

Example 6

Study of the Degradation Mechanism of the Compound of Formula 1

Figure 6:
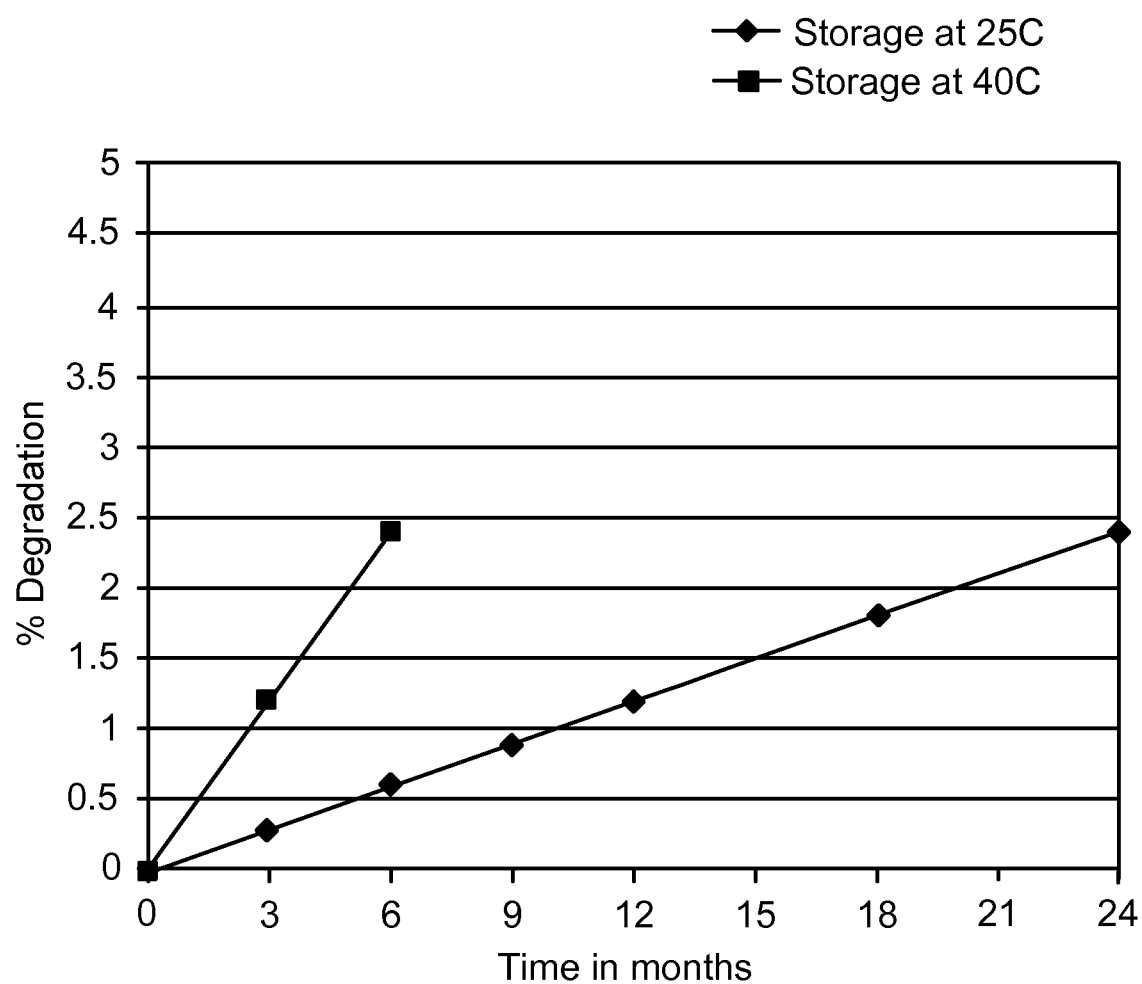
FIG. 6 shows the stability of the compound of Formula 1 by showing the % degradation of the compound of Formula 1 over time upon storage at 25° C. and 40° C.
Figure 7:
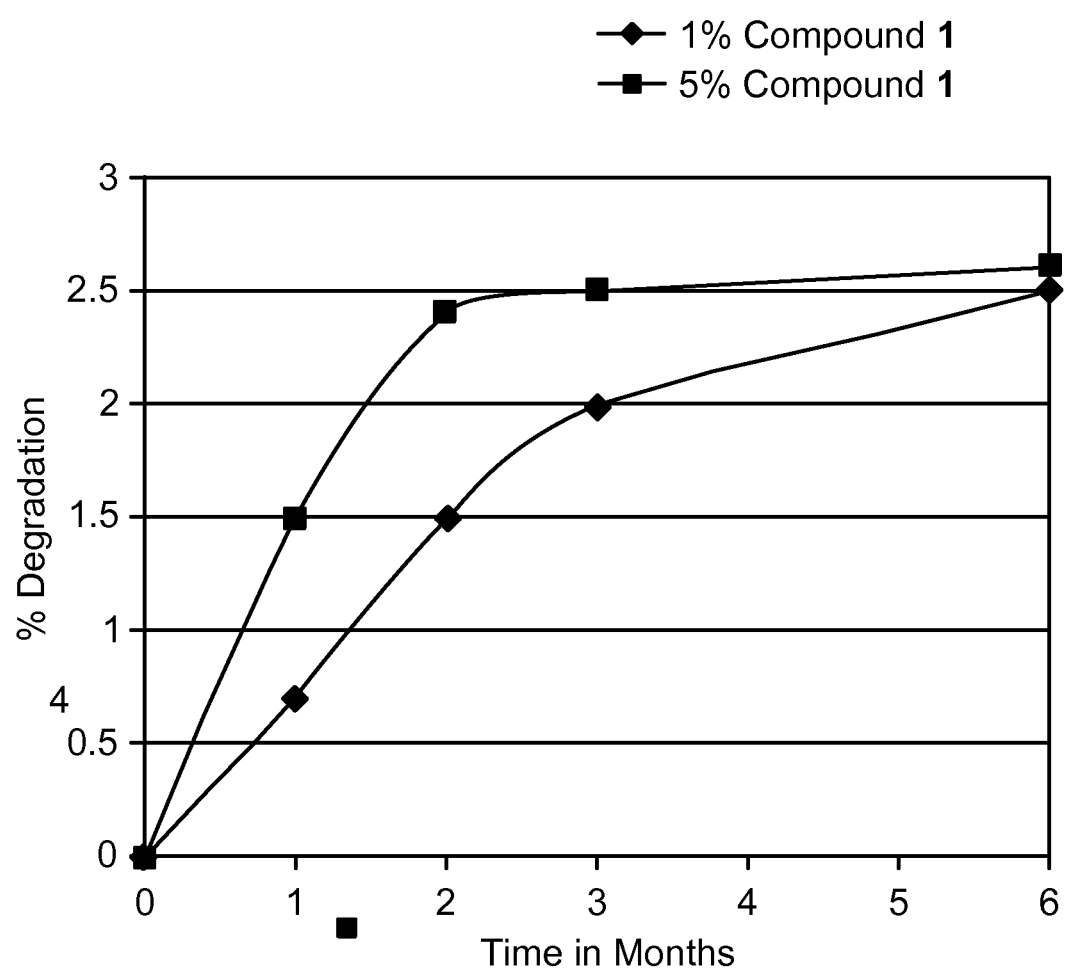
FIG. 7 shows degradation profiles of the compound of Formula 1 over time at a concentration of 1% w/v and 5% w/v.

FIG. 6 shows the typical degradation profile of compounds when degradation occurs via reactions like X→Y or X→Y+Z. The degradation profile of the compound of Formula 1 was prepared by monitoring the total percentage degradation of 1.0% and 5.0% w/v solutions of 1 after about every four weeks for a period of six months. The results of these experiments are graphically represented in FIG. 7. The rate of degradation of the 5.0% w/v solution of 1 was greater than the rate of degradation of the 1.0 w/v solution of 1. Both the solutions appear to reach the same level of degradation when a limiting reactant, such as oxygen concentration is reduced. These results indicate that degradation of the compound of Formula 1 might be a result of its reaction with oxygen.

Example 7

Effect of Sparging with Nitrogen on the Stability of the Formulations of the Compound of Formula 1

Figure 8:
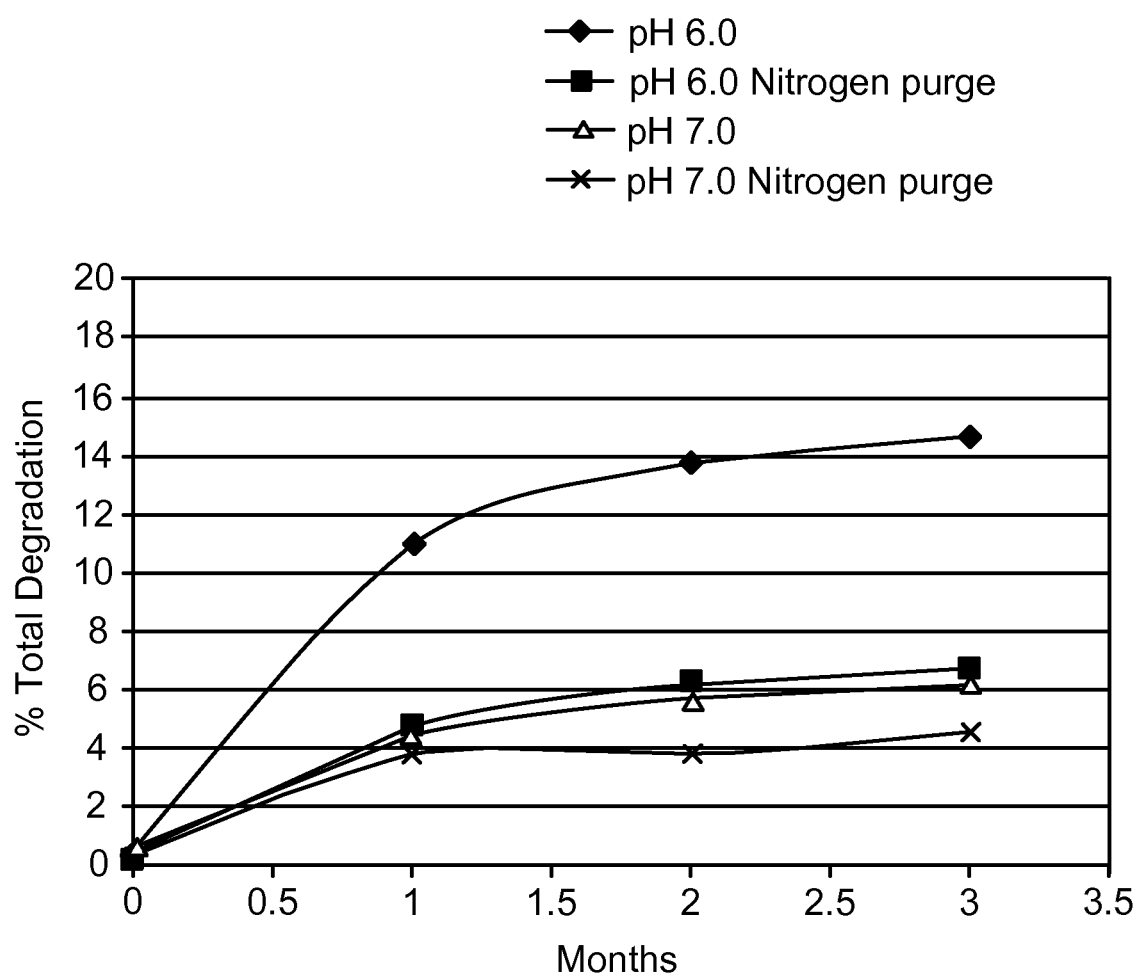
FIG. 8 shows the effect of sparging on % total degradation for a solution of the compound of Formula 1 with nitrogen to remove oxygen at various pHs.

Four separate solutions of the compound of Formula 1 were prepared. The pH of the first solution was buffered to 6.0. The pH of the second solution was also buffered to 6.0 and the solution was additionally sparged with nitrogen. The pH of the third solution was buffered to 7.0. The pH of the fourth solution was also buffered to 7.0 and the solution was further sparged with nitrogen. All the four solutions were stored at a temperature of about 40° C. for a period of about four months. The percentage of total degradates was measured for each solution after about every four weeks. The results of this experiment are graphically represented in FIG. 8. The solutions sparged with nitrogen exhibited better stability in comparison to the solutions not sparged with nitrogen. Also the solutions at pH 7.0 exhibited improved stability over the corresponding solutions at pH 6.0, suggesting that pH is a critical variable for stability of Formula 1.

Example 8

Effect of pH on Stability of Nitrogen Sparged Solutions of the Compound of Formula 1

Figure 9:
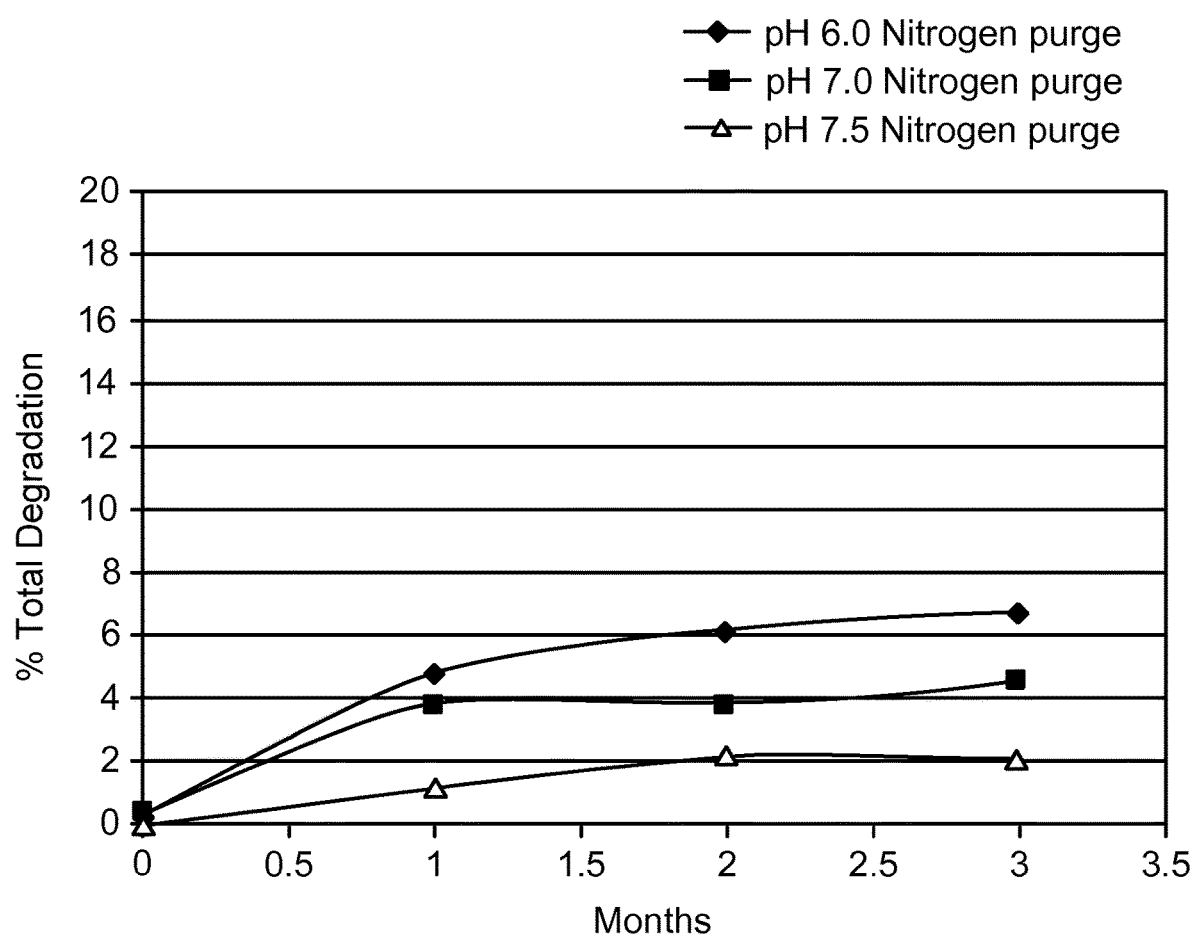
FIG. 9 shows the effect of pH on stability of the compound of Formula 1 with nitrogen sparged solutions at various pH over time.

Three solutions of the compound of Formula 1 were prepared. The pH of the first solution was buffered to 6.0, the pH of the second solution was also buffered to 7.0 and pH of the third solution was buffered to 7.5. All the three solutions were sparged with nitrogen were stored at a temperature of about 40° C. for a period of about four months. The percentage of total degradates was measured for each solution after about every four weeks. The results of this experiment are graphically represented in FIG. 9. The nitrogen sparged solutions with higher pH exhibited improved stability.

Example 9

Effect pH on Stability of Formulation of the Compound of Formula 1 Further Comprising of One or More Antioxidants

Figure 10:
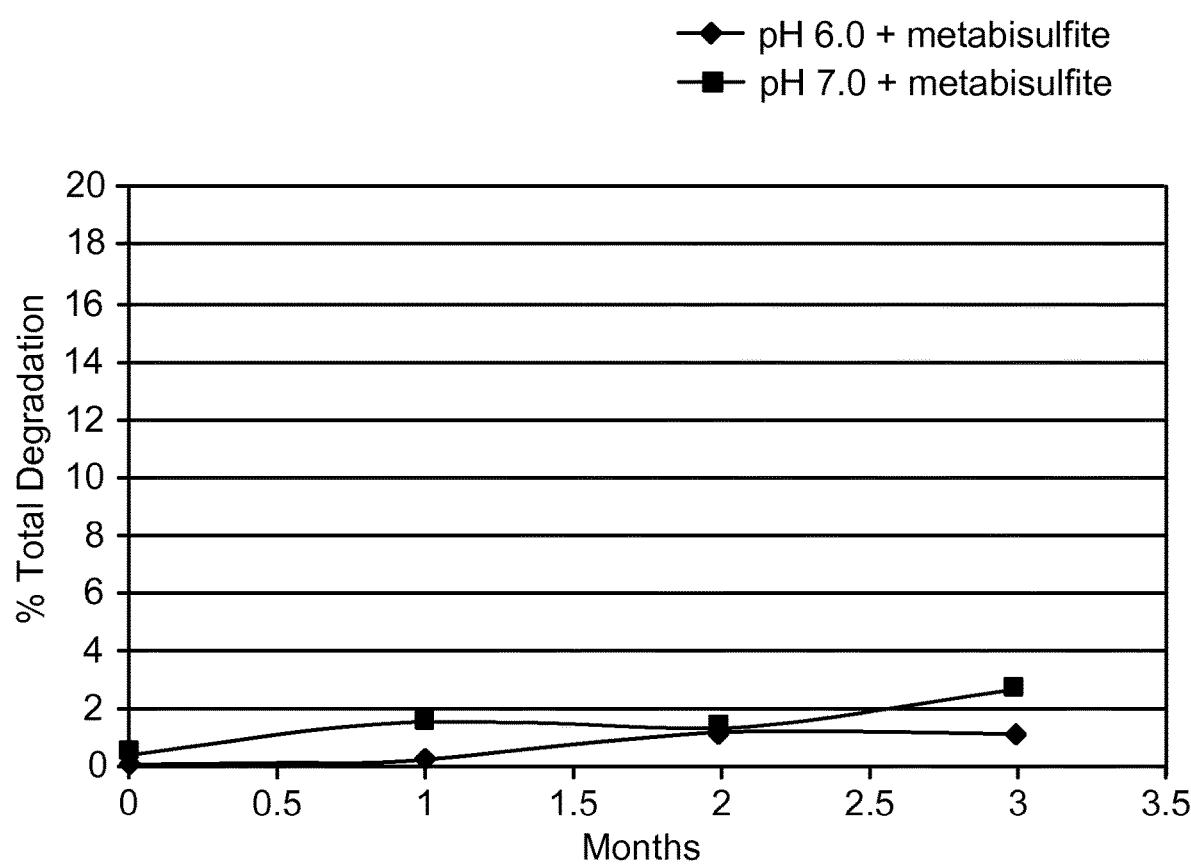
FIG. 10 shows the effect of antioxidant and pH on stability of the compound of Formula 1 by showing the % total degradation over time.

Two solutions of the compound of Formula 1 were prepared. The pH of the first solution was buffered to 6.0 and the pH of the second solution was also buffered to 7.0. A metabisulfite salt was added to both the solutions and were stored at a temperature of about 40° C. for a period of about four months. The percentage of total degradates was measured for each solution after about every four weeks. The results of this experiment are graphically represented in FIG. 10. These results show that the addition of an antioxidant significantly reduces both the degradation of Formula 1 and the sensitivity of the stability of Formula 1 to pH.

Example 10

Effect of Antioxidants on the Formulations of the Compound of Formula 1

Figure 11:
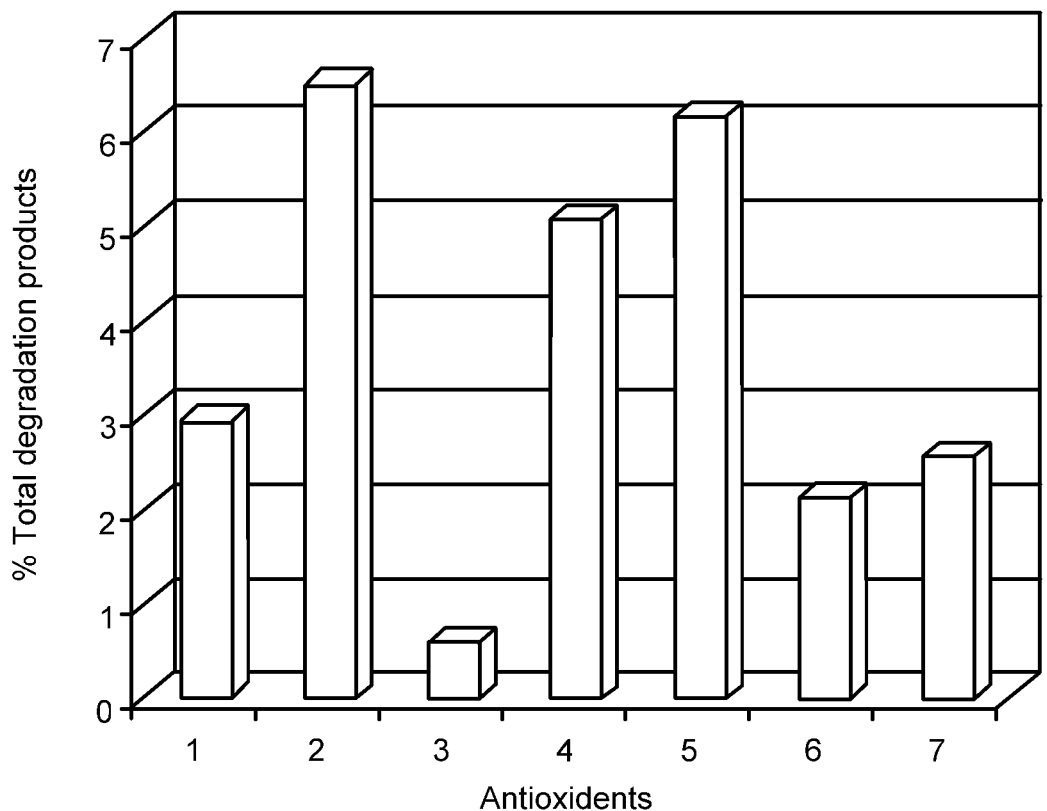
FIG. 11 shows the effect of antioxidants on the stability of the compound of Formula 1 by showing the % total degradation products after storage at pH 6.5 at 40° C. for one month with various antioxidants.

Seven different solutions of Formula 1, buffered at a pH of about 6.5, were prepared. Sodium bisulfite (0.2% w/v) and sodium thiosulfate (0.3% w/v) were added to the first solution, sodium bisulfite (0.2% w/v) was added to the second solution, sodium thiosulfate (0.3% w/v) was added to the third solution, acetylcysteine (0.2% w/v) was added to the fourth solution, thioglycerol (0.2% w/v) was added to the fifth solution, Vitamin E TPGS (053% w/v) was added to the sixth solution, and ascorbic acid (0.3% w/v) was added to the seventh solution. All solutions were stored at a temperature of about 40° C. for a period of about one month after which the percentage of total degradates was measured for each solution. The results of this experiment are graphically represented in FIG. 11. Surprisingly, the solutions containing sodium thiosulfate alone exhibited the best overall stability.

Example 11

Effect pH on Stability of Nitrogen Sparged Solutions

Figure 12:
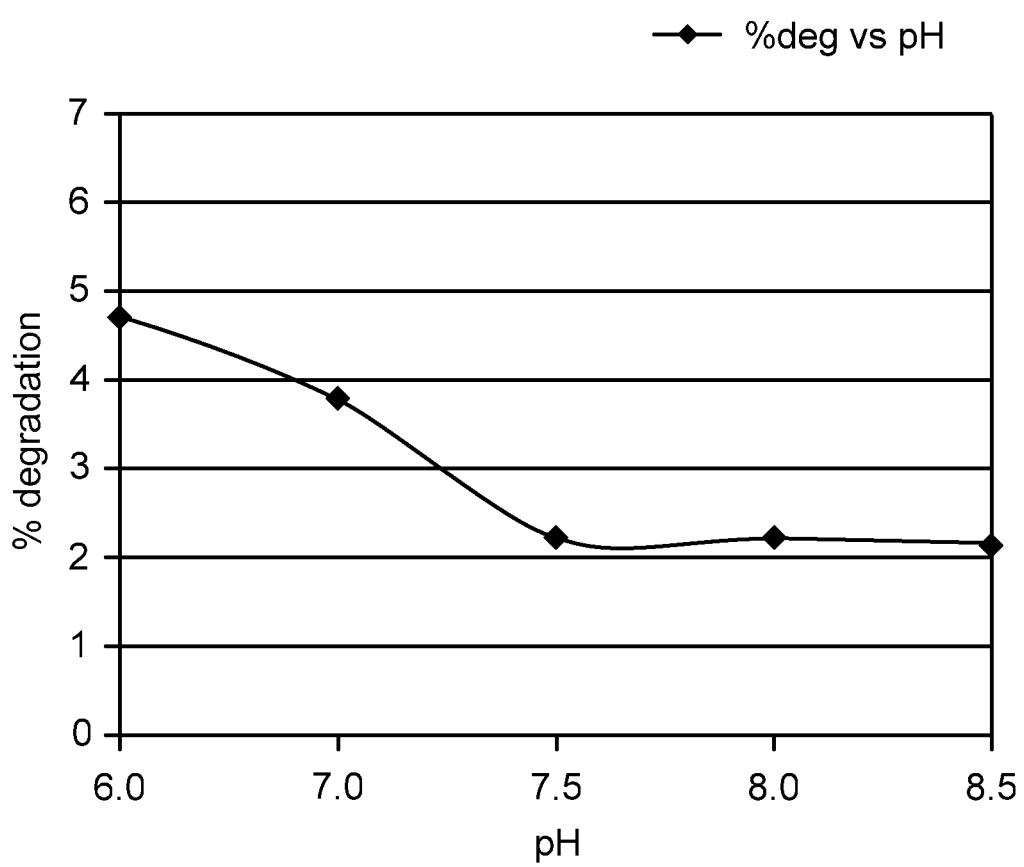
FIG. 12 shows the effect of pH on stability of the compound of Formula 1 with nitrogen sparged solutions at various pHs after storage at 40° C. for one month in the absence of antioxidant components.

Five different solutions of the compound of Formula 1 were prepared. The first solution was buffered to a pH of 6.0, the second solution was buffered to pH 7.0, the third solution was buffered to pH 7.5, the fourth solution was buffered to pH 8.0, and the fifth solution was buffered a pH of 8.5. No antioxidant was added and all solutions were stored at a temperature of about 40° C. for a period of about one month after which the percentage of total degradates was measured for each solution. The results of this experiment are graphically represented in FIG. 12. The solutions at higher pH exhibited better stability.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A composition comprising a compound of Formula 1:

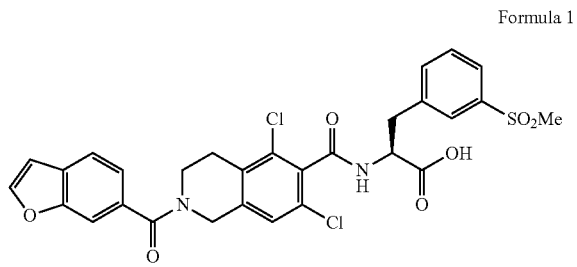 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

Formula 1 or a salt thereof,
a pharmaceutically acceptable carrier, and
a thiosulfate salt,
wherein the composition has less than about 1% of total degradation products of the compound of Formula 1 when stored at a temperature of about 40° C. for a period of at least one month.

2. The composition of claim 1, wherein the pharmaceutically acceptable carrier is an aqueous carrier.

3. The composition of claim 2, wherein the thiosulfate salt is present in an amount of about 0.01% to about 0.5% w/v.

4. The composition of claim 2, wherein the thiosulfate salt is present in an amount of about 0.3% w/v.

5. The composition of claim 3, wherein the thiosulfate salt is sodium thiosulfate.

6. The composition of claim 5, wherein the composition is buffered to a pH of about 6.0 to about 8.5.

7. The composition of claim 6, wherein the compound of Formula 1 is present in an amount of about 1% to about 5% w/v.

8. The composition of claim 7, wherein the compound of Formula 1 is present in an amount of about 5% w/v.

9. The composition of claim 8, wherein the composition exhibits less than about 1% of total degradation products of the compound of Formula 1 upon storage at a temperature of about 40° C. for a time period selected from the group consisting of 2 months, 3 months, 4 months, 5 months, and 6 months.

10. The composition of claim 8, further comprising a sparged nitrogen gas.

11. The composition of claim 1, comprising:
about 5% w/v of the compound of Formula 1;
about 0.3% w/v thiosulfate salt;
sodium chloride; and
sodium phosphate,
wherein the composition has a pH of about 7.0 to about 8.0.

12. The composition of claim 11, wherein the sodium phosphate is dibasic sodium phosphate.

13. A composition comprising:
4 to 10 w/v % compound of Formula 1:

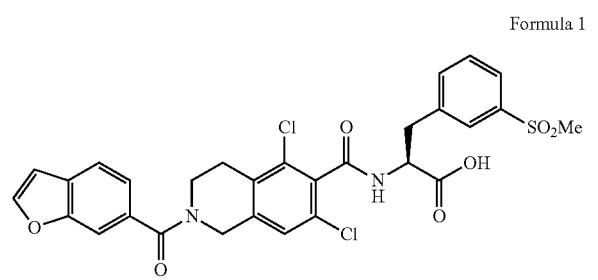 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

Formula 1 or a salt thereof; and
0.2 to 0.4% antioxidant, the antioxidant being sodium thiosulfate;

wherein the composition is an aqueous solution with the compound of Formula 1 dissolved therein, and
wherein the composition is suitable for topical administration to the eye.

14. A composition comprising:
about 5 w/v % compound of Formula 1:

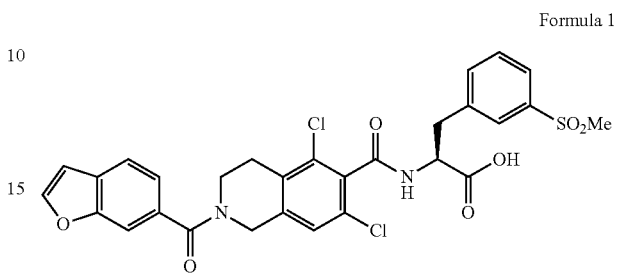

Formula 1 or a salt thereof;
about 0.3% w/v antioxidant, the antioxidant being sodium thiosulfate;
sodium phosphate for buffering the compositions at a pH of 6.0 to 8.0; and
sodium chloride for providing isotonicity to the composition;
wherein the composition is an aqueous solution having the compound of Formula 1 dissolved therein, and
wherein the composition is suitable for topical administration to the eye.

15. The composition of claim 13, wherein said thiosulfate salt is the primary antioxidant.

16. The composition of claim 13, further comprising a sparged inert gas.

17. The composition of claim 16, wherein the sparged inert gas is nitrogen.

18. The composition of claim 13, wherein the composition is buffered to a pH of about 7.5.

19. The composition of claim 1, wherein the composition comprises one or more antioxidants and a sparged inert gas.

20. The composition of claim 1, wherein the formulation expires in about 1-5 years when stored at or below ambient temperature.

21. The composition of claim 14, wherein the formulation expires in about 1-5 years when stored at or below ambient temperature.

* * * * *